United States Patent [19]
Dietz

[11] 4,356,065
[45] Oct. 26, 1982

[54] POLAROGRAPHIC OXYGEN CONCENTRATION SENSOR AND METHOD OF DETERMINING OXYGEN CONTENT IN THE EXHAUST GASES OF AN INTERNAL COMBUSTION ENGINE

[75] Inventor: Hermann Dietz, Gerlingen, Fed. Rep. of Germany

[73] Assignee: Robert Bosch GmbH, Stuttgart, Fed. Rep. of Germany

[21] Appl. No.: 213,049

[22] Filed: Dec. 4, 1980

Related U.S. Application Data

[63] Continuation of Ser. No. 6,093, Jan. 4, 1979, abandoned, which is a continuation-in-part of Ser. No. 885,368, Mar. 13, 1978, abandoned.

[30] Foreign Application Priority Data

Mar. 18, 1977 [DE] Fed. Rep. of Germany ....... 2711880

[51] Int. Cl.³ .......................................... G01N 27/58
[52] U.S. Cl. ................... 204/1 T; 123/489; 204/195 S
[58] Field of Search ............ 204/195 S, 1 S; 60/276; 73/26; 422/98; 123/489

[56] References Cited

U.S. PATENT DOCUMENTS

| | | | |
|---|---|---|---|
| 3,411,073 | 11/1968 | Marr | 324/33 |
| 3,691,023 | 9/1972 | Ruka et al. | 204/1 T |
| 3,820,015 | 6/1974 | Jeunehomme | 324/33 |
| 4,097,353 | 6/1978 | Kishida et al. | 204/195 S |
| 4,132,616 | 1/1979 | Tantram et al. | 204/195 P |
| 4,158,166 | 6/1979 | Isenberg | 204/195 S X |

OTHER PUBLICATIONS

H. Dietz et al., "Electrochemical Sensors for the Analysis of Gases", pp. 3-90, (1977).
John O'M Bockris et al., "Modern Electrochemistry", vol. 2, pp. 1074-1079, (1970).

*Primary Examiner*—G. L. Kaplan
*Attorney, Agent, or Firm*—Frishauf, Holtz, Goodman & Woodward

[57] ABSTRACT

A solid electrolyte is sandwiched between a measuring electrode exposed to the gas and a reference electrode exposed to a reference gas of known oxygen level, and a cover, for example in form of a layer or a cap, is applied over the measuring electrode. To linearize output from the sensor over a wide range of oxygen partial pressure in a gas so that, upon applying a voltage across the electrodes thereof, current flow will be representative of the oxygen concentration in the gas, the cover consists of a material having a predetermined diffusion resistance to oxygen while essentially inhibiting convection of gases to the electrode and limiting the quantity of oxygen reaching the measuring electrode to that value at which any oxygen molecules reaching the measuring electrode will be immediately converted by electrode reaction, thus inhibiting current flow through the sensor due to diffusion of gases and preventing that the current through the sensor will be determined by the activating energy of the charge penetration through the phase separation at the electrode surface.

8 Claims, 3 Drawing Figures

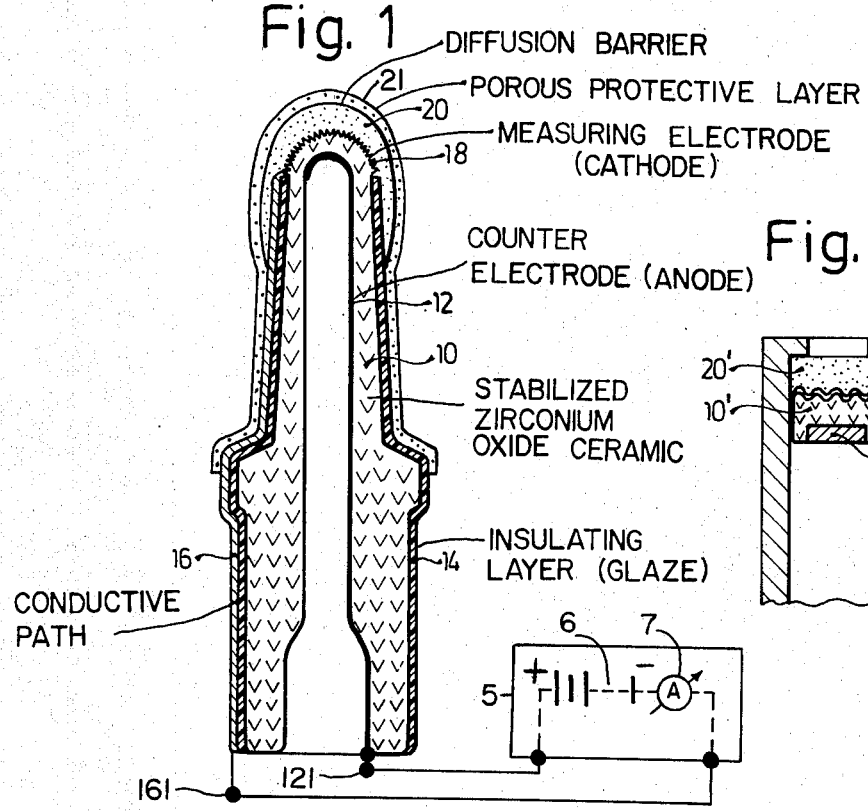
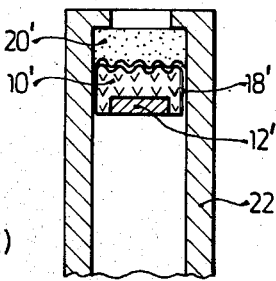
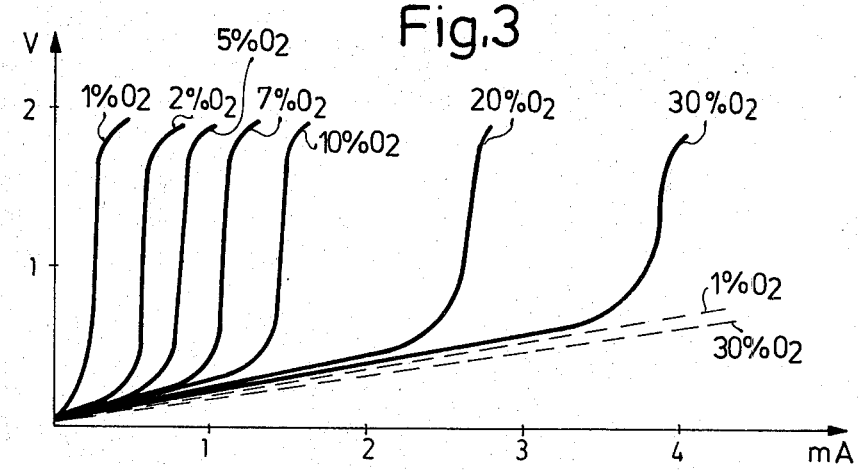

POLAROGRAPHIC OXYGEN CONCENTRATION SENSOR AND METHOD OF DETERMINING OXYGEN CONTENT IN THE EXHAUST GASES OF AN INTERNAL COMBUSTION ENGINE

This is a continuation of application Ser. No. 006,093, filed Jan. 4, 1979 which in turn was a continuation-in-part of application Ser. No. 885,368, filed Mar. 13, 1978 and both now abandoned.

Reference to related patents assigned to the assignee of the present invention:

U.S. Pat. No. 4,021,326, Pollner et al; U.S. Pat. No. 3,841,987, Friese et al; U.S. Pat. No. 3,960,692, Weyl et al; and to U.S. Pat. No. 3,691,023, Ruka and Panson.

The present invention relates to a polarographic sensor to determine the concentration of oxygen in gases, and more particularly the concentration of oxygen in the exhaust gases from internal combustion engines.

BACKGROUND AND PRIOR ART

Various types of sensors using a solid electrolyte which responds to the oxygen concentration of a gas with respect to a reference oxygen concentration, for example free air, are known; in one such structure, see for example U.S. Pat. No. 4,021,326, a voltage is generated which depends on whether the sensor senses oxygen or not. Customarily, the structure includes a solid electrolyte which has a gas permeable measuring electrode applied to one face thereof, which face is exposed to the gas to be tested; the other face of the solid electrolyte has a gas permeable counter electrode applied which is exposed to the reference gas of known oxygen concentration. The solid electrolyte, thus, is sandwiched between the two electrodes.

Another type of sensor is described in U.S. Pat. No. 3,691,023, Ruka and Panson. Such sensors are known as polarographic sensors. The determination of the oxygen concentration is obtained by evaluating the diffusion limiting current upon application of a voltage across the electrodes thereof. This diffusion limiting current is derived as a combination of the following:

If a substance, the concentration of which is to be determined, is used up due to electrode reaction, then concentration of this substance at the electrode surface becomes zero if the polarization is sufficient, that is, if a polarization or bias voltage of suitable value is applied between the measuring electrode and the counter electrode. Each particle of the respective substance is immediately converted at the measuring electrode. If the reaction of the charge penetration at the electrode surface can proceed without interference, then the quantity of the substance reaching the electrode surface alone determines the speed with which the reaction will proceed, and hence the current flowing between the electrodes. These conditions, as described in the measuring of concentration of a quantity in gases in the aforementioned U.S. Pat. No. 3,691,023 is met only if the material, the concentration of which is to be determined, is present in very small quantities. Consequently, the sensor described in the aforementioned U.S. patent can measure oxygen concentration only up to a partial oxygen pressure of less than $10^{-6}$ atmospheres. If the oxygen concentration rises above this level, the diffusion limiting current which can be theoretically expected becomes so high that the level of the current being measured is no longer determined by the quantity of oxygen which reaches the measuring electrode, but rather by the activating energy of the charge penetration due to the phase boundaries occurring at the surface of the electrode.

Sensors to determine the oxygen content in exhaust gases, that is λ—sensors, have previously been proposed in which a gas permeable cover coating is applied to a catalytically active measuring electrode. Such a cover coating is used to protect the measuring electrode with respect to contamination, particularly to protect the electrode against deposits of lead and other contaminants found in the exhaust gases of internal combustion engines due to the types of fuel used. The cover coating is porous with rather coarse pores. Such coarse pores permit free passage of the gas to be sensed while, however, mechanically protecting the surface of the catalytically active measuring electrode.

The Invention

It is an object to provide a sensor of the polarographic type to sense oxygen concentration in which the level of oxygen which can be sensed is substantially higher than that in known sensors of this type, and which provides reliably reproducible analog outputs from gases to be tested even if the oxygen concentration is much higher than heretofore capable of being sensed by such sensors.

Briefly, the basis sensor structure of a sandwich of a measuring electrode, a solid electrolyte body and a reference electrode is retained; in accordance with the invention, the measuring electrode is covered with a coating, or with a cover applied thereto, which has predetermined diffusion resistance with respect to oxygen.

The basic concept of the invention thus consists in limiting the quantity of the oxygen which reaches the measuring electrode by means of this additional cover to such values that, after the electrodes have a voltage thereacross, any oxygen molecule which migrates to, and reaches the measuring electrode is immediately converted by electrode reaction. The current which will flow between the electrodes of the sensor will have a value determined solely by the amount of oxygen molecules reaching the electrode after diffusion through the cover. In other words, the quantity of gas and hence the oxygen therein diffused towards the sensor electrode itself is throttled or reduced to such an extent that migration conditions will occur which are comparably to measuring oxygen concentration in liquids in which the diffusion speed is reduced by a factor of about $10^5$.

The sensor is particularly suitable to measure oxygen concentration in the exhaust gases from internal combustion engines, typically automotive-type internal combustion engines, which are operated, at least part of the time, with a fuel-air mass ratio (λ) which deviates from a value of unity (λ=1) and which varies in wide ranges, for example $0.8 < \lambda < 1.8$ in Otto engines and $1 < \lambda < 8$ in Diesel engines. λ-sensors, as previously proposed, are not suitable to determine the oxygen concentration in exhaust gases with such wide variations of the fuel-air ratio since the sensing voltage is logarithmically dependent on partial oxygen pressure. In actual practice therefore, it is possible only to evaluate the substantial jump in output voltage when the value of λ changes from just below unity to just above unity, that is, upon change between plus and minus of slight variations about λ=1. Coatings previously proposed to protect the sensing electrode against mechanical damage or contamination by contaminants and residues in the exhaust from the engine are not capable of suppressing the results of convection at the measuring electrode—as is desired by the structure in accordance with the present invention—since the porosity of the coating is much too coarse.

Drawings, illustrating preferred examples:

FIG. 1 is a highly schematic longitudinal cross-sectional view through the sensing portion of a sensor in accordance with the present invention;

FIG. 2 is a schematic longitudinal cross-sectional fragmentary view through a sensor constructed in accordance with another embodiment; and, FIG. 3 shows a family of graphs of current (abscissa) vs. voltage (ordinate), showing the relationships for various oxygen contents which occur in a sensor constructed in accordance with the present invention.

Only so much of the sensor is shown in FIG. 1 as is necessary for an understanding of the present invention; the remaining structural features may, for example, be as described in the related referenced patents.

A solid electrolyte body 10 made, for example, of stabilized zirconium oxide ceramic ($ZrO_2$) is formed as a tube closed at one end, in which the closed end of the tube is exposed to the gas or gas mixture to be tested or sensed. The interior of the tube of the body 10 has a counter electrode 12 applied thereto made, for example, of platinum. The outside of body 10 is covered with an insulating layer 14 up to about the rounded tip thereof. The rounded tip is left free of insulation material. The insulation material 14 preferably is an insulating glaze, at the outside of which a conductive path 16 is applied which leads to the tip of the sensor. A measuring electrode 18 made of an inert metal, such as platinum, is applied to the outside of the closed end of the solid electrolyte ceramic body 10. The measuring or sensing electrode 18 is connected to the conductive path 16. It can be applied to the body 10 by any suitable and known process, for example by vapor deposition, by chemical deposition, by applying as a paste and subsequent firing, by plasma spraying, or the like; any one of these processes can be used to apply a thin coating of platinum forming the measuring or sensing electrode 18 to the tip of the body 10. The sensing electrode 18 is comparatively thin and has a comparatively large surface.

In accordance with the invention, a cover or coating 20 is provided for the measuring electrode 18. This cover or coating 20 is made of a material which has a predetermined diffusion flow resistance with respect to oxygen to control migration of oxygen molecules. The cover 20 must completely cover the outside of the sensing electrode 18.

Various methods can be used to apply the cover 20 over the electrode 18.

Example 1: Somewhat coarser, not spreading (upon flowing) spinel with an average grain diameter of about 50 $\mu$m is applied by means of plasma spraying up to a thickness of about 0.3 mm. Thereafter, a second relatively thick layer of about 2 mm thickness is applied thereover, the second layer being derived from readily flowable fine-grained spinel having an average grain diameter of about 10 $\mu$m.

Example 2: A preformed cap, fitting over the end or tip portion of the sensor, that is, over the electrode 18 applied to the body 10, is made of a material which has the desired diffusion characteristics. This cap is then secured above the electrode 18. The attachment should be such that the cap which forms the coating or cover just touches the surface of the measuring electrode 18 without leaving any appreciable voids.

The sensor of FIG. 2 is, as a general principle, constructed similarly to that of FIG. 1. Only the geometric shapes of the elements differ, and similar components have been given similar reference numerals, with prime notation. The ceramic 10' is sandwiched between the counter or reference electrode 12' and the sensing or measuring electrode 18'. The cover 20', in the form of a coating or a cap, as well as the body 10 and the electrodes are all shaped to be disk-like. The sensing end is secured in a tube 22 which holds the sensing cell formed by elements 10', 12', 18, 20' in assembled relation and permits exposure of the cell to a stream of gases to be tested. The housing sleeve 22 can be made of metal and may, for example, directly form the conductor 16, that is, one terminal of the cell; the electrode 12' can then be connected to a suitable connector carried out of the center of the tube 22. Alternatively, the tube 22 can be made of non-conductive material with a separate conductive path thereon, in electrically conductive connection with electrode 18'. A biassing voltage is applied between the electrodes 12, 18, or 12', 18'. The outer form of the body 10' can be ridged or corrugated, for example in the form of concentric grooves to further increase the surface area thereof. The cover 20' then will have matching corrugations.

It is important that the cover of the measuring electrode is of a material having fine or very small pores, that is, pores of a size so small that practically no convection of gas will occur. A layer of such fine pores can consist of spinel, aluminum oxide, or another suitable ceramic material. It must be temperature resistant since the solid electrolyte operates at the high temperatures of exhaust gases directly obtained from an internal combustion engine. Due to the presence of the layer with the fine, small pores, the gas must first diffuse through this layer or, rather, pass through the pores of this layer in order to reach the surface of the sensing electrode 18, 18', respectively. This layer with the fine pores is thus provided to prevent convection of gas, or, in other words, forms a leak barrier, in which the leakage is strictly controlled. This is obtained by decreasing the diffusion cross section and additionally by decreasing the length of the diffusion flow path so that migration of oxygen molecules is so controlled that, even at higher oxygen partial pressures, the limiting current will be substantially below the exchange current, that is, the kinetic value for reversible charge exchange and charge passage at an electrode. The pores should be so small that the diffusion of oxygen therethrough alone determines the speed of the electrode reaction.

The layer 20, 20', with the fine pores therein, is provided to decrease the migration cross section; it must not, however, similarly decrease the effective electrode surface. This is obtained, for example, as above described, by making the cover of two different layers in which the outer one, for example, is very dense and has only a few and small pores; whereas the inner one has a porous structure which decreases the effective electrode surface as little as possible. Consequently, in the preferred form, the barrier layer with the fine pores is not immediately applied against the electrode surface. That can be obtained by making the cover either as a preformed cap of suitable shape and composition of the inside and of the electrode, and by selection of the particular process with which the cap is secured to the electrode.

The sensor with the cap, as described, applied thereto is highly sensitive as is apparent from the family of curves of FIG. 3. The current, measured by ammeter 7, which will flow with respective oxygen concentrations, varying over a wide range, is shown with respect to applied polarization voltage or bias voltage derived from battery 6. The sensor tested and yielding the graphs of FIG. 3 has a cover of spinel of about 2 mm thickness applied to the measuring electrode 18 or 18'.

The electrodes 12, 16 are connected to suitable terminals 12', 16' which, in turn, are connected to an evaluation circuit 5 which provides the bias voltage, shown schematically by the battery 6 and the current measuring instrument, shown schematically by the ammeter 7. Of course, the ammeter 7 can be a transistorized current amplification circuit providing an output signal representative of the current flow through the sensor upon application of the battery bias voltage.

Other materials than spinel may be used for the cover 20, 20'. Suitable materials are: aluminum oxide, Mg-Al-silicates or mixtures thereof with each other or with the spinel mentioned above, or tirconium dioxide or another suitable ceramic material. These materials, preferably, are also applied in multiple layers, or in such a way that the substantial thickness of the material is of a rather fine-grain structure; the grain structure, however, becoming coarser towards the electrode so that little of the active electrode surface is lost. The thickness of the fine-grain structure, preferably, is in the order of about 1 to 2 mm, particularly for the materials given above, although it may be somewhat greater, or less. The preferred thickness of the coarser layer is about 0.2 mm, although the thickness is not critical and a range of from 0.15 to ½ mm is generally suitable. If materials of higher diffusion resistance than spinel are used, then the outer layer may be only 0.3 to 1 mm, and an inner, coarser layer of 0.15 mm will be sufficient.

FIG. 3 shows an additional curve, in broken line, which illustrates the performance of a sensor in accordance with the prior art. As can be seen, the curves for high oxygen concentration and for low oxygen concentration are so close together that meaningful decoding of output to determine oxygen concentration is extremely difficult. The wide range of current variation with variation of the oxygen content in gases in accordance with the present invention is clearly apparent from a comparison of the broken-line curves of the prior art structure with those of the solid-line curves of the structure of the present invention.

A porous protective layer 21 (see cross-referenced U.S. Pat. No. 4,021,326, Pollner et al) may be applied over the cover 20, 20' as a mechanical protection and to prevent contamination of the cover 20, 20'. Likewise, the end of the sensor can be enclosed in a protective shield tube.

FIG. 3 clearly illustrates the relationship of increasing current with increasing oxygen concentration and also shows that there is a range at about 1 to 1.5 V where the current will experience an essentially linear rise, with respect to voltage, at a given oxygen concentration, so that minor variations in voltage will not affect measuring accuracy.

The type of sensor disclosed, for example, in U.S. Pat. No. 4,021,326, Pollner et al, determines, essentially, whether the sensor is operating in an oxidizing or in a reducing atmosphere. In contrast, the sensor in accordance with the present invention, can provide an analog output of actual oxygen concentration. The family of curves of FIG. 3 can be obtained only, however, if the flow of gases or, rather, migration of oxygen molecules to the electrode is sufficiently throttled to control the speed of the consequent reaction and, hence, the value of the current which flows. Only under such conditions will the sensor operate under diffusion limited current operation conditions, which are analog dependent on oxygen concentration.

To permit measuring of oxygen partial pressures greatly in excess of those described in the referenced U.S. Pat. No. 3,691,023, Ruka et al, flow of oxygen molecules to the electrodes must be so controlled that is the diffusion resistance greater than the polarization resistances at the electrode, so that the diffusion of oxygen at the electrode alone determines the speed of the reaction, and hence the extent of current flow measured in instrument 7. In accordance with the present invention, flow of oxygen is throttled to such extent that the diffusion resistance at the electrode is then increased to such an extent that substantially higher concentrations than those previously believed capable of measurement can be determined.

The flow diffusion resistance is determined by the geometry of the diffusion layer 20. A thick barrier-and-diffusion layer will require a low porosity, and hence result in a low limiting current. Fine pores and/or a long diffusion path will effect a high diffusion resistance. The length of the flow path, of course, is in part determined by the thickness of the layer 20. Under stationary conditions, and when pure diffusion results, a convection-free diffusion layer in the vicinity of the electrode will result in a limiting current $I_{lim}$ which is proportional to the concentration C of the component to be converted—in this case oxygen—in accordance with the following relationship:

$$I_{lim} = z \cdot F \cdot D \cdot (q/d) \cdot C \quad (1)$$

in which $z \cdot F$ is the charge converted in the electrode reaction—per mol; for oxygen, $z=4$ and F is the Faraday constant (defined as the quantity of electricity associated with 1 gram—equivalent of chemical change, that is, 96,500 coulombs.) D is the diffusion coefficient; the fraction is a geometric factor in which q is the diffusion cross section and d is the diffusion length. The diffusion cross section is determined by the number and size of the pores in the diffusion layer. The diffusion length is determined by the length of the continuous pores, in which this diffusion length is related to the thickness of the layer 20 and a deviation or detour path length.

Diffusion limit current conditions were found at permeabilities of from $5 \cdot 10^{-5}$ to $5 \cdot 10^{-2}$ bar ml/sec cm, preferably from $10^{-4}$ to $10^{-3}$ bar ml/sec cm, measured at the insulating layer with 1 bar pressure difference. The permeabilities were obtained with porous ceramic layers having an average pore radius of from 0.01 to 50 $\mu$m and a thickness layer of from 0.2 to 2 mm.

I claim:

1. Polarographic oxygen concentration sensor to sense concentration of oxygen in gas exhaust from a combustion engine having
    a solid electrolyte body (10, 10') shaped to provide two oppositely located surfaces;
    a gas permeable first electrode (18, 18') applied to one surface of the body, said first surface being adapted to be exposed to the gas in which the oxygen concentration is to be sensed;

a second gas permeable electrode (12, 12') applied to the other surface of the body (10, 10'), said second surface being adapted to be exposed to a reference gas having a known concentration of oxygen, whereby the body will be intermediate said electrodes (18, 12) and separate the test gas and the reference gas;

means (6, 127, 161) applying a voltage across said electrodes to cause a current to flow in dependence on the electrode reaction with oxygen in the gas reaching said first electrode in the range of between about $\frac{1}{2}$ to $1\frac{1}{2}$ volts;

means (7) obtaining a signal representative of said current flow;

and a cover (20, 20', 21) over the first electrode (18) comprising a porous, solid material permitting flow, or diffusion of gases therethrough;

said cover, in accordance with the invention, comprising a two-layer structure having an outer porous protective layer (21) and an inner layer (20, 20') forming a gas flow barrier to permit migration of only a controlled quantity of oxygen molecules therethrough and thereby limit the quantity of oxygen molecules reaching said first electrode (18, 18'), said inner layer of the cover being characterized by being of such porosity and thickness that the relationship of cross section of the pores and path length for oxygen molecules with respect to the diffusion limited current at the first electrode is defined by $$I_{lim} = z \cdot F \cdot D \cdot (q/d) \cdot C$$

wherein $I_{lim}$ is the limit current; $z \cdot F$ the charge conversion by the electrode reaction, z defining the charge conversion for oxygen and being equal to 4; F is the Faraday constant; D the diffusion coefficient; q the diffusion cross section; d the diffusion length; and C the concentration of oxygen in the gas.

2. Sensor according to claim 1, wherein the cover (20, 20') comprises spinel, or zirconium dioxide.

3. Sensor according to claim 1, wherein said inner layer of the cover comprises a plasma sprayed coating applied directly on the first electrode (18, 18').

4. Sensor according to claim 1, wherein the cover (20') comprises a preformed cover cap applied to said first electrode (18').

5. Method of obtaining an analog electrical output representative of oxygen in exhaust gas from a combustion engine having an electrochemical cell exposed to the sample gas, said cell having a solid electrolyte body (10, 10') shaped to provide two oppositely located surfaces;

a gas permeable first electrode (18) applied to one surface of the body;

a second gas permeable electrode (12) applied to the opposite surface of the body (10, 10'), whereby the body will be intermediate said electrodes (8, 12)

comprising the steps of supplying said gas, the oxygen concentration of which is to be sensed, to the first electrode;

providing an oxygen environment at said second electrode;

applying a voltage across said first and second electrodes at a level in the range of about $\frac{1}{2}$ to $1\frac{1}{2}$ volts;

controlling the magnitude of said voltage to establish said electrochemical cell in a diffusion limited current mode of operation, wherein variations in the oxygen partial pressure of the gas, the oxygen concentration of which is to be determined and to which the first electrode is exposed, produces changes in electrochemical cell current;

measuring said current as an indication of the oxygen partial pressure of said gas;

and including the further step of limiting the quantity of oxygen molecules migrating to, and reaching said first electrode (18, 18') to that value at which any oxygen molecule, within the gas reaching said first electrode, is immediately converted by electrode reaction, by throttling access of said gas to said first electrode (18), said throttling step comprising passing said gas through a flow or migration resistance path having a path-limiting current relationship defined by:

$$I_{lim} = z \cdot F \cdot D \cdot (q/d) \cdot C$$

wherein $I_{lim}$ is the limit current, $z \cdot F$ the charge conversion by the electrode reaction, z defining the charge conversion for oxygen and being equal to 4; F is the Faraday constant; D the diffusion coefficient; q the diffusion cross section; d the diffusion length; and C the concentration of oygen in the gas;

to effect immediate conversion by electrode reaction of any oxygen molecules migrating to, and reaching said first electrode (18, 18');

and protecting said flow or migration resistance path by passing the gas flow through a porous protective path layer (21) prior to said throttling step, the flow resistance of the gas flow through the protective path layer being less than the flow resistance upon passage of said gas in said throttling step.

6. Method according to claim 5, wherein the step of providing said flow resistance path comprises applying a cover (20) over the first electrode (18) of a porous material having an oxygen molecule migration characteristic therethrough that oxygen molecules reaching said first electrode (18, 18') are immediately converted by electrode reaction and the speed of the resulting electrochemical reaction, and hence diffusion limited current flow, will be entirely determined by the concentration of oxygen in said sample gas.

7. Polarographic oxygen concentration sensor to sense concentration of oxygen in exhaust gas from a combustion engine having a solid electrolyte body (10, 10') shaped to provide two oppositely located surfaces;

a gas permeable first electrode (18, 18') applied to one surface of the body, said first surface being adapted to be exposed to the gas in which the oxygen concentration is to be sensed;

a second gas permeable electrode (12, 12') applied to the other surface of the body (10, 10'), said second surface being adapted to be exposed to a reference gas having a known concentration of oxygen, whereby the body will be intermediate said electrodes (18, 12) and separate the test gas and the reference gas;

means (6, 127, 161) applying a voltage across said electrodes to cause a current to flow in dependence on the electrode reaction with oxygen in the gas reaching said first electrode;

means (7) obtaining a signal representative of said current flow;

and a cover (20) over the first electrode (18) comprising a porous, solid material permitting flow, or diffusion of gases therethrough;

said cover, in accordance with the invention, comprising a two-layer structure having an outer porous protective layer (21) and an inner layer (20, 20') forming a gas flow barrier to permit migration of only a controlled quantity of oxygen molecules therethrough and thereby limit the quantity of oxygen molecules reaching said first electrode (18, 18'), said cover being characterized by being of such porosity and thickness that the relationship of cross section of the pores and path length for oxygen molecules with respect to the diffusion limited current at the first electrode is defined by $$I_{lim} = z \cdot F \cdot D \cdot (q/d) \cdot C$$

wherein $I_{lim}$ is the limit current; $z \cdot F$ the charge conversion by the electrode reaction, z defining the charge conversion for oxygen and being equal to 4; F is the Faraday constant;

D the diffusion coefficient; q the diffusion cross section; d the diffusion length; and C the concentration of oxygen in the gas.

8. Method of obtaining an analog electrical output representative of oxygen in exhaust gas from a combustion engine, having an electrochemical cell exposed to the sampe gas, said cell having a solid electrolyte body (10, 10') shaped to provide two oppositely located surfaces;

a gas permeable first electrode (18) applied to one surface of the body;

a second gas permeable electrode (12) applied to the opposite surface of the body (10, 10'), whereby the body will be intermediate said electrodes (8, 12)

comprising the steps of supplying said gas, the oxygen concentration of which is to be sensed, to the first electrode;

providing an oxygen environment at said second electrode;

applying a voltage across said first and second electrodes;

controlling the magnitude of said voltage to establish said electrochemical cell in a diffusion limited current mode of operation, wherein variations in the oxygen partial pressure of the gas, the oxygen concentration of which is to be determined and to which the first electrode is exposed, produces changes in electrochemical cell current;

measuring said current as an indication of the oxygen partial pressure of said gas;

and including the further step of limiting the quantity of oxygen molecules migrating to, and reaching said first electrode (18, 18') to that value at which any oxygen molecule, within the sample gas reaching said first electrode, is immediately converted by electrode reaction, by throttling access of said sample gas to said first electrode (18), said throttling step comprising passing said gas through a flow of migration resistance path having a path-limiting current relationship defined by:

$$I_{lim} = z \cdot F \cdot D \cdot (q/d) \cdot C$$

wherein $I_{lim}$ is the limit current, $z \cdot F$ the charge conversion by the electrode reaction, z defining the charge conversion for oxygen and being equal to 4; F is the Faraday constant; D the diffusion coefficient; q the diffusion cross section; d the diffusion length; and C the concentration of oxygen in the gas;

to effect immediate conversion by electrode reaction of any oxygen molecules migrating to, and reaching said first electrode (18, 18');

and protecting said flow or migration resistance path by passing the gas flow through a porous protective path layer (21) prior to said throttling step, the flow resistance of the gas flow through the protective path layer being less than the flow resistance upon passage of said gas in said throttling step.

* * * * *